US012582419B2

(12) United States Patent
Daly et al.

(10) Patent No.: US 12,582,419 B2
(45) Date of Patent: Mar. 24, 2026

(54) TIBIAL SUPRAPATELLAR ENTRY PORTAL SYSTEM

(71) Applicant: ORTHOXEL DAC, Cork (IE)

(72) Inventors: Charles Daly, County Cork (IE); Gerard Kiely, County Cork (IE); Sean O'Callaghan, County Cork (IE); Richie Gough, County Cork (IE)

(73) Assignee: ORTHOXEL DAC, Cork (IE)

( * ) Notice: Subject to any disclaimer, the term of this patent is extended or adjusted under 35 U.S.C. 154(b) by 520 days.

(21) Appl. No.: 17/999,580

(22) PCT Filed: May 26, 2021

(86) PCT No.: PCT/EP2021/064087
§ 371 (c)(1),
(2) Date: Nov. 22, 2022

(87) PCT Pub. No.: WO2021/239829
PCT Pub. Date: Dec. 2, 2021

(65) Prior Publication Data
US 2023/0200828 A1     Jun. 29, 2023

(30) Foreign Application Priority Data
May 28, 2020    (EP) .................................... 20177277

(51) Int. Cl.
*A61B 17/17*     (2006.01)
*A61B 17/34*     (2006.01)
*A61B 17/56*     (2006.01)

(52) U.S. Cl.
CPC ...... *A61B 17/1717* (2013.01); *A61B 17/1764* (2013.01); *A61B 17/3468* (2013.01); *A61B 2017/3488* (2013.01); *A61B 2017/564* (2013.01)

(58) Field of Classification Search
CPC ............ A61B 17/1764; A61B 17/1767; A61B 17/1717; A61B 2017/0268
See application file for complete search history.

(56) References Cited

U.S. PATENT DOCUMENTS

| | | | |
|---|---|---|---|
| 9,566,078 B2 | 2/2017 | Hirsch et al. | |
| 2013/0190570 A1* | 7/2013 | Hirsch ................... | A61B 17/34 600/204 |
| 2013/0310886 A1 | 11/2013 | Vanosten | |
| 2014/0081281 A1 | 3/2014 | Felder | |
| 2018/0353193 A1 | 12/2018 | Hirsch et al. | |

FOREIGN PATENT DOCUMENTS

| | | |
|---|---|---|
| EP | 2797521 B1 | 12/2015 |
| EP | 3466357 A1 | 4/2019 |

OTHER PUBLICATIONS

International Search Report and Written Opinion in corresponding Application No. PCT/EP2021/064087, dated Sep. 22, 2021, (22 pages).

* cited by examiner

*Primary Examiner* — Olivia C Chang
(74) *Attorney, Agent, or Firm* — Bookoff McAndrews, PLLC

(57) ABSTRACT
A tibial suprapatellar entry portal system (1) comprising a sleeve (2), an anchor pin (200), and a trocar (40).

19 Claims, 12 Drawing Sheets

TIBIAL SUPRAPATELLAR ENTRY PORTAL SYSTEM

FIELD OF THE INVENTION

The invention relates to a tibial suprapatellar entry portal system. In particular, the invention relates to a tibial suprapatellar entry portal system that includes a guide sleeve and a handle for suprapatellar surgery.

BACKGROUND TO THE INVENTION

Fractures of the tibia can be difficult and awkward to treat as the patient's knee is typically flexed at about 90° so the surgeon can access to the top of the tibia and insert an intramedullary nail, for example, in particular to treat proximal or segmental fractures where fracture reduction is difficult or hampered by the flexion of the knee and the resulting forces applied by the patella on the proximal portion of the fractured tibia.

While infrapatellar insertion of the intramedullary nail into the tibia had been the preferred option since the 1940s, the required hyperflexion of the leg produced unintended problems. Firstly, obtaining a starting point location in the proximal end of the tibia using fluoroscopy needed significant tilting of the C-arm. This was often limited by the bottom of the operating table and often caused issues with locating an adequate starting point. Secondly, the pull of the quadriceps as well as the posteriorly directed nail caused flexion in the proximal segment, which could cause procurvatum deformity.

Many techniques have been developed over time to combat these problems and in 1996 a new technique described a semi-extended position with the knee at approximately 15° to 20° flexion as a potential solution to the problem. This allowed lateral mobilisation of the patellar permitting easy access to a starting point, with maintained relaxed extensor mechanism. Building on this many surgeons proposed techniques that would complement this approach and in 2010 a described technique using the leg in the previous described position but creating the incision suprapatellar and passing the tools needed to create an opening in the proximal tibia behind the patella and through the patellofemoral joint. This created easier access to the proximal tibia without having the leg muscles tensed and also allowed for easier imaging using the C-arm as it did not need to be tilted as much. A way to protect the patella from damage during the obtaining of access to the proximal tibia starting point and the use of opening reaming through the patellofemoral joint gave rise to the need of a protection sleeve instrument, to protect the patella.

U.S. Pat. No. 9,566,078 describes a sleeve comprising an elastic material which has a longitudinal axis and comprises a first end, a second end, an inner surface, a flexible outer surface and at least two grooves that extend at the inner surface from the first end to the second end, and wherein the grooves are adapted to accommodate elongated fixation elements. The elongated fixation elements may, for example, be realized as wires (e.g., so-called K-wires), nails or pins.

EP 2797521 describes a system for inserting and securing, through a suprapatellar region of a leg, a nail into a medullary canal of a bone, the system comprising a flexible sleeve configured to flex so as to change a shape of the first axis from a first configuration to a second configuration and further comprises a retaining member configured to support at least a portion of the flexible sleeve in the leg, wherein the retaining member is configured to position the flexible sleeve through the suprapatellar region of the leg such that the flexible sleeve leading end is aligned with a proximal end of the bone.

The problems with the guide sleeves described above and currently being used is that they are difficult to assemble due to multiple components, difficulty in separating the sleeve from the internal member, a complicated mechanism for removing the internal guide/trocar and can only anchor in one direction.

It is an object of the present invention to overcome at least some of the above-mentioned problems.

SUMMARY OF THE INVENTION

The inventors have developed a tibial nail that also includes a stainless-steel instrument for a suprapatellar entry surgical approach. The tibial suprapatellar and retrograde entry portal system is a substantially elliptical single piece that can be anchored in position to help retain the system during the nail implantation procedure and to facilitate ease of use. The design of the system also aids with speeding up the procedure. The anchoring technique used by the suprapatellar entry portal system of the claimed invention allows for tailoring of the insertion system fixation by the surgeon.

In practice, this means that the surgeons can anchor the insertion system to either the tibia, femur or both.

Clinically, the claimed invention provides a protective sleeve to allow reamers, guidewires and entry wires pass through, to open the end of the medullary canal, and ream the intramedullary canal shaft. The reason for anchoring using up to three anchor pins (a first anchor pin, a second anchor pin, and a third anchor pin) at three different anchoring points is that while the reaming is taking place, there is no movement of the system and this prevents the sharp edge of the reamer interfacing unnecessarily with the anatomy of the subject. The use of three anchor points allows the system to be adapted for use in all patient's anatomy.

The system is designed to be inserted bi-directionally through the patellofemoral joint and allows the anchor points to be used in reverse). When the system is activated via tibial entry, the third anchor pin anchors in the femur, while when the system is activated via femoral entry, the third anchor pin anchors to the tibia.

According to the present invention there is provided a tibial suprapatellar entry portal system (1) comprising a sleeve (2), an anchor pin (200), a trocar (40), and an entry wire, wherein the sleeve (2) comprises a sheath (2a) and a sleeve handle (20); the sheath (2a) having a proximal end (5) with an entry port (6) and a distal end (4) having an exit port (77) separated by a longitudinal body (3) having an outer surface (3a), an inner surface (3b), and an internal shaft (3c), and at least two grooves or circular cannulations (7a, 8a) extending from the proximal end (5) to the distal end (4) between the outer surface (3b) and inner surface (3a) of the longitudinal body (3), and wherein the sheath (2a) is rigid. Typically, the sleeve (2) has a substantially elliptical outline.

In one aspect, the proximal end (5) further comprises portals (7,8) configured to access the circular cannulations (7a, 8a) and a securing means (9) configured to engage with the trocar (40). The circular cannulations (7a, 8a) provide the user with deployment certainty of the anchor pin placement and prevents the anchor pins from "wandering" while anchoring the system in place.

In one aspect, the proximal end (5) further comprises a third anchor point (11). The use of the third anchor point means that the anchor points are offset in two planes, which adds greater anchoring certainty and retention. The combination of anchor points would allow a surgeon to move the leg of a subject to reduce the fracture without the protective sleeve moving relative to the tibia. In one aspect, the third anchor point (11) is offset at about 5° to 11° in the X plane relative to the coronal plane, and about 7° to 13° in the Y plane relative to the transverse plane, allowing securement of the third anchor pin to the femur during tibia suprapatellar use and the tibia during retrograde use. In one aspect, the third anchor point (11) is offset at about 6° to 10° in the X plane relative to the coronal plane, and about 8° to 12° in the Y plane relative to the transverse plane, allowing securement of the third anchor pin to the femur during tibia suprapatellar use and the tibia during retrograde use. In one aspect, the femoral anchor point is offset firstly about 8 degrees in the X plane relative to the coronal plane and then about 10 degrees in the Y plane relative to the transverse plane to give a correct trajectory to the femur when the leg is positioned correctly. When the three anchor points are used, the sheath (2a) tip position is kept in contact with the bone, at the angle set in the sagittal plane by the user, to allow reaming during use.

In one aspect, the circular cannulations (7a, 8a) are parallel to the longitudinal axis of the body (3). In one aspect, the circular cannulations (7a, 8a) are convergent from the proximal end (5) to the distal end (4). In one aspect, the circular cannulations (7a, 8a) are divergent from proximal end (5) to the distal end (4).

In one aspect, the body (3) further comprises a channel (50) running parallel with and in communication with the circular cannulation (7a) or circular cannulation (8a). Preferably, the channel (50) runs in a medial-lateral plane relative to the sleeve handle (20) and divides the sheath (2a) into a first body component part (2b) and a second body component part (2c). When the first and second body component parts (2b, 2c) divide apart, either one of the body component parts (2b, 2c) can be removed and the remaining body component part (2b or 2c) acts as a patellar shield from an intramedullary nail. Typically, the anterior component part is removed, that is, the component part that is on the patella side.

In one aspect, the channel (50) is closed, and the first and second body component parts (2b, 2c) of the sheath (2a) are re-joined, when the sleeve handle (20) and a locking mechanism (30) are assembled together with the sheath (2a). Preferably, when the channel (50) opens, the first and second body component parts (2b, 2c) divide apart, and the locking mechanism (30) is disassembled from the sleeve (2). Preferably, the locking mechanism (30) comprises a female member (32) configured to engage with a male member (24a) attached to the proximal end (23) of the sleeve handle (5).

In one aspect, the sleeve handle (20) comprises a grip (21), a distal end (22), a proximal end (23) and a mating means (24) attached to the proximal end (23). Preferably, the mating means (24) is typically the male member (24a) that is configured to engage with a female member (32) of the locking mechanism (30). Ideally, the male member (24a) further comprises a threaded portion (26) which is configured to mate with an equivalent threaded portion within the female member (32) of the locking mechanism (30). Ideally, the male member (24a) comprises two threaded portions (26a,b) spaced apart by a smooth surfaced area (27).

In one aspect, the locking mechanism (30) comprises a substantially circular body (31) having the female member (32) on one side thereof and a vacuum tube connection member (33) on the opposite side, and an indentation (10) adapted to receive a mating means (24) and create a mechanical or friction hold with the sheath (2a) to secure the locking mechanism (30). Preferably, the substantially circular body (31) is configured to comprise a hinge forming a hinged clasp. Preferably, the locking mechanism (30) further comprises a stop mechanism actuated by a sliding mechanism or a spring-loaded plunger and pin mechanism.

In one aspect, the sleeve handle (20) is adjustable to swivel about 180° around the locking mechanism (30). The swivelling nature of sleeve handle (20) around 180 degree allows either left- or right-handed users use the system with ease, or for use with either left or right legs. The swivelling nature of the sleeve handle (20) also allows the user to access the release button easily and ensures that the release button does not get pressed by mistake during use.

In one aspect, the trocar (40) comprises an insertion guide (42) at a proximal end thereof and a tip (43) at a distal end thereof, separated by a longitudinal body (41). Preferably, the insertion guide (42) comprises at least one entry point guide (44) at the proximal end.

As mentioned above, the third anchor point is offset at about 5° to 11° in the X plane relative to the coronal plane, and about 7° to 13° in the Y plane relative to the transverse plane, allowing securement of the third anchor pin to the femur during tibia suprapatellar use and the tibia during retrograde use, to give a correct trajectory to the femur when the leg is positioned correctly. When the three anchor points are used, the combination of the three anchor points allows the surgeon to move the patient's leg to reduce the fracture without the sleeve moving relative to the tibia.

In one aspect, there is provided a method for using the tibial suprapatellar entry portal system (1) as described above, the method comprising the steps of: attaching the sleeve (2) to the locking mechanism (30) in the orientation for either right or left leg; locking the sheath (2a) in place by tightening the threaded portion (26) of the sleeve handle (20) in the female member (32) of the locking mechanism (30); sliding the trocar (40) into the shaft (3c) of the sheath (2a) so that the securing means (9) is activated and engages the trocar (40); and inserting the sleeve (2) fully into the patellofemoral joint until it comes into contact against a proximal end of the tibia.

In one aspect, the method further comprises the step of pressing the securing means (9) on the sheath (2a) to unlock and remove the trocar (40) from the shaft (3c) and, if required, inserting the trocar (40) fully into the shaft (3c).

In one aspect, the method further comprises the step of inserting a first entry wire into the at least one entry point guide (44) and into the proximal end of the tibia. In one aspect, the method further comprises the step of turning and offsetting the at least one entry point guide (44) to select the correct location to place a second entry wire. In one aspect, the method further comprises the step of inserting a second entry wire into the at least one entry point guide (44) offset to the selected position relative to the first entry wire; and optionally, removing the incorrectly positioned first entry wire and recentre the sleeve (2) and the trocar (40) over the correctly positioned second entry wire. In essence, if a user places the first entry wire and is not happy with its position, the additional entry point guide (44) on the trocar (40) allows the controlled offset, and then the first entry wire is taken out as it is not needed anymore.

In one aspect, the method further comprises releasing the securing means (9) and pushing the sleeve (2) forward to engage a distal end of the sheath (2a) with the tibia while maintaining the trocar (40) in position.

In one aspect, the method further comprises the step of inserting a first and second anchor pin (200) into circular cannulations (7a, 8a) in the sheath (2a), and into the proximal end of the tibia or femur. Preferably, the method further comprises inserting a third anchor pin (200) into the third anchor point (11).

In one aspect, once the first and second anchor pin (200) are inserted into the circular cannulations (7a, 8a) in the sleeve (2), the trocar (40) is removed from the shaft (3c). Preferably, a third anchor pin (200) is inserted into the third anchor point (11) and into the femur. The combination of anchor points would allow a surgeon to move the leg of a subject, for example, when reducing the fracture, without the protective sleeve moving relative to the tibia.

In one aspect, when the locking mechanism (30) is loosened the body component parts (2b, 2c) come apart to form the channel (50) in the sheath (2a) and an intramedullary nail is passed through the central shaft (3c).

It should be noted that after the sheath (2a) splits into the first body component part (2b) and the second body component part (2c), the system allows for an intramedullary nail to pass through, where the user may wish to allow the sheath (2a) (when not split) or one of the body component part (2b, 2c) that is anterior to the patella when the sheath (2a) splits, could be left in situ and the nail would pass under it, thus protecting the patella from contact with the nail or insertion instruments.

In one aspect, the anchor pin (200) comprises a shoulder (202) that, when the anchor pin (200) is inserted into the circular cannulations (7a, 8a), creates a mechanical hard stop by contacting the top surface of the portals (7,8) of the proximal end (5) of the sheath (2a), and secures the distal end of the sheath (2a) rigidly against the tibia or the femur.

In one aspect, the anchor pin (200) has a distal diameter that is accommodated within the circular cannulations (7a, 7b) and a larger proximal diameter that butts against trocar (40). Preferably, the distal diameter of the anchor pin (200) is fully threaded or partially threaded.

In one aspect, there is provided a kit of parts for use in repairing a bone fracture, the kit comprising the tibial suprapatellar entry portal system (1) as described above.

The thickness of the wall between the outer surface and inner surface of the sheath (2a) is between about 0.1 mm to about 2.0 mm, preferably about 0.2 mm to about 1.5 mm, more preferably between about 0.4 mm and 1.4 mm, and ideally about 0.6 mm to about 1.2 mm. The wall of the sleeve is rigid. This rigidity aids in accommodating the trocar within the sleeve.

In one aspect, the sleeve is composed of a durable yet rigid material allowing for cleaning and reprocessing after clinical use, for example, polypropylene, polyethylene (PE), polyethylene terephthalate copolymer (PETG), amorphous polyethylene terephthalate (APET), stainless steel and titanium. Preferably, the material is stainless steel, titanium, or a combination thereof.

In one aspect, the anchor pins or entry wires are composed of stainless steel or titanium.

In use, briefly, the trocar is inserted into the central shaft of the sleeve having the open channel to form the assembly of the invention. The assembly is then passed into the patellofemoral joint. The entry point guide allows for correct placement of the first entry wire using the suprapatellar approach. The first entry wire is inserted through the central cannulation of the entry point guide of the trocar and into the proximal end of the tibia. The position is checked using a C-arm, if the position is incorrect the trocar can be rotated so that one of the offset entry point guides are in the correct position. A second entry wire is inserted into the correctly positioned offset entry point guide to provide a correctly positioned entry point. One correctly positioned the sleeve is anchored to the tibia and femur by placing up to three anchors pins in the anchor points of the sleeve. The trocar is removed from the assembly. A channel reamer is passed through the central shaft and the canal of the tibia is reamed out. The channel reamer is then removed. The anchor pins are then removed from the tibia and femur. The locking mechanism and the handle are removed from the assembly. The sleeve can now "split" open to form the two separate sleeve parts in the patellofemoral joint to enlarge the central shaft. An intramedullary nail is then allowed to pass through the central shaft while the sleeve still protects the patella from damage caused during nail insertion. The nail is inserted into the tibia and the two-part sleeve can then be removed from the patellofemoral joint. In one embodiment the anchor pin(s) may remain in situ with a part(s) of the sleeve during nail passage.

The sleeve and locking mechanism are made from metal and slide into one another in clearance. A threaded portion attached to the handle is threaded through a corresponding female member in the locking mechanism and presses against an indentation in the sleeve, creating a mechanical or friction hold with the sleeve. A trocar is then slid through the central shaft of the sleeve, pushing a spring ledge of the securing mechanism in the proximal end of the sleeve out of the way (that is, compressing it). When the trocar is fully engaged, the spring ledge of the securing means aligns with a slot in the trocar allowing the spring ledge of the securing means to decompress and engage with the trocar slot, holding it in position. The securing means on the anterior side of the sleeve, when pushed, compresses the spring ledge and allows the trocar to be removed.

The advantages of the claimed invention are, for example:

Entry tube axis fixation of the anchor pins, through the insertion system and into the top of the tibia, wedges the system against the top of the tibia and prevents back out by creating a physical barrier.

The system can also be used for retrograde insertion and can be placed posterior to the patellofemoral joint from superior to interior. The user can still use three anchor points when inserted in the retrograde direction.

Reduced risk of reaming debris entering knee as protection system is physically secured to the tibia.

Anchoring allows the surgeons to have both hands free to complete other surgical steps.

Using rigid metal anchor pins and insertion system shaft prevents any rotational movement of the system during use.

The presence of an angled hole, relative to the entry tube axis, in the insertion system allows for simultaneous anchoring of the system into both the tibia and femur. This prevents rotational or axial movement of the system during use.

The anchoring system is fixed in the X, Y, and Z planes when the three anchoring points are used, which restricts any tilting movement as well as preventing rotation and axial movement.

The presence of both tibial and femoral anchoring techniques provides a choice for the surgeon on their preferred method of anchoring (tibial or femoral). It also allows the surgeon to adapt the anchoring to suit the patient's anatomy.

Easy for the surgeon to use as the assembly and disassembly of components has been intuitively designed. The ergonomically positioned spring button on the system allows for a quick release and automatic lock of the trocar and wire guide, meaning they can be seamlessly inserted and removed from the system.

Assembly and disassembly of instrument is quick and reliable.

Ergonomic atraumatic tip and sleeve profile to protect patellar on entry and exit of the system.

Handle can be adjusted ergonomically for right or left leg insertion before use, meaning one system can be used for the right or left tibia.

Definitions

In the specification, the term "anchor pins", "securing wire", "k-wire", "entry wire" or "reaming wire" should be understood to mean elongated fixation elements that fix the system to the tibia or femur. The anchor wires are typically used for fixing the sleeve in position, while the k-wire/entry wire are typically used for centring on the tibia to ream over. The k-wire or entry wire is smooth and has a consistent diameter throughout its length, while the anchor pin has a shoulder (see below) and is typically shorter than the k-wire or entry wire.

In the specification, the term "sleeve handle" should be understood to mean the handle that is attached to the sleeve of the tibial suprapatellar entry portal system.

In the specification, the term "rigid metal" should be understood to mean that the instrument material will always hold its shape and position and will not bend during use. In technical material terms, this is also called stiffness and refers to the elasticity of the material. Preferred materials are stainless steel titanium, or a combination thereof.

In the specification, the term "relative to the entry tube axis" should be understood to mean where the femoral anchor point of the system is at an angle of between about 5° to 13° relative to the central shaft of the sleeve in the vertical axis. Preferably, the femoral anchor point is an at angle of about 7°, 8°, 9°, 10°, 11° or 12° relative to the central shaft in the horizontal axis.

In the specification, the term "locking mechanism" should be understood to mean that the handle and sleeve are assembled together to generate a rigid assembly that will not accidentally or easily become unlocked during use. Furthermore, after use the components of the locking mechanism can be easily disassembled for cleaning and replacement in the required kit.

In the specification, the term "mating means" should be understood to mean, a method where two instrument assembly together to provide defined position of the components. In this case the male member is the sleeve and female member the handle, they can only be assembled with the handle always 90 degrees to the sleeve axis which broadly allows the handle to sit in the transverse plane with the sleeve axis in the coronal plane.

In the specification, the terms "groove" and "circular cannulation", which can be used interchangeably, should be understood to mean that the groove/cannulation is adapted to accept the anchor pins/wires.

BRIEF DESCRIPTION OF THE DRAWINGS

The invention will be more clearly understood from the following description of an embodiment thereof, given by way of example only, with reference to the accompanying drawings, in which:—

8

Figure 1:
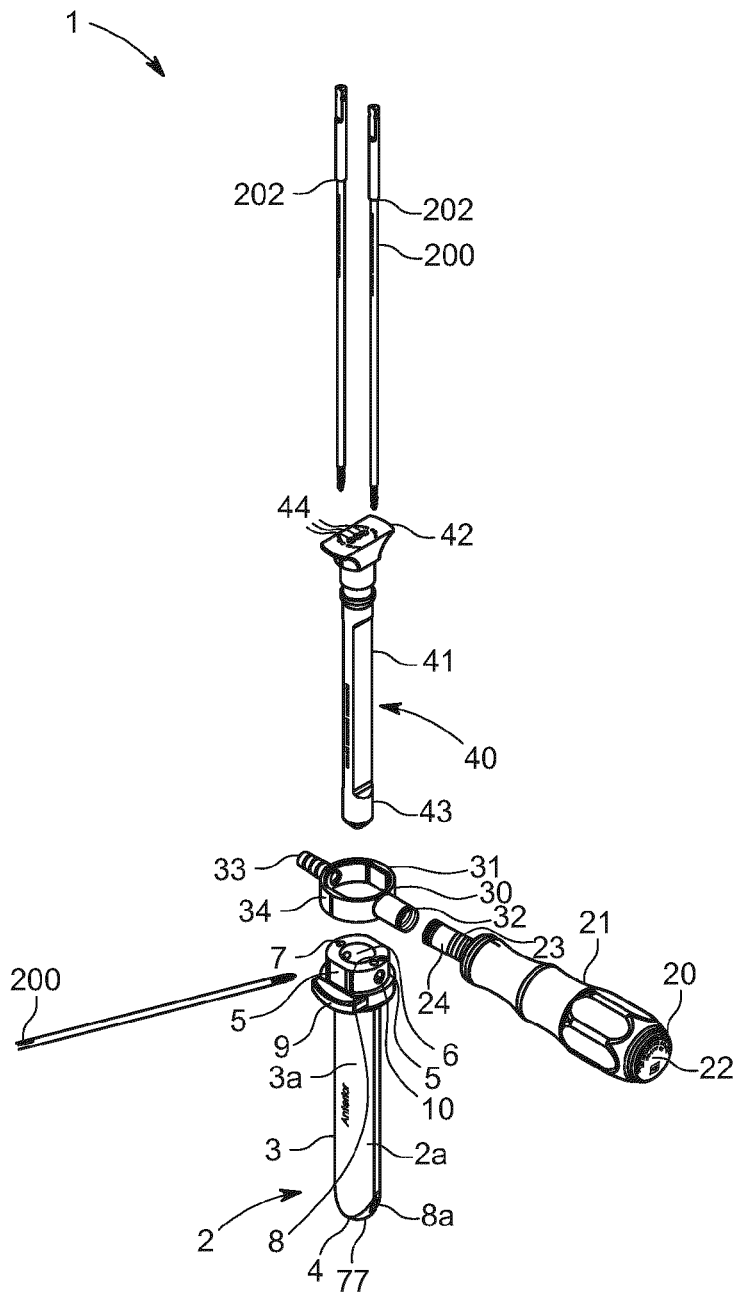
FIG. 1 illustrates an exploded view of the tibial suprapatellar entry portal system of the claimed invention.
Figure 2:
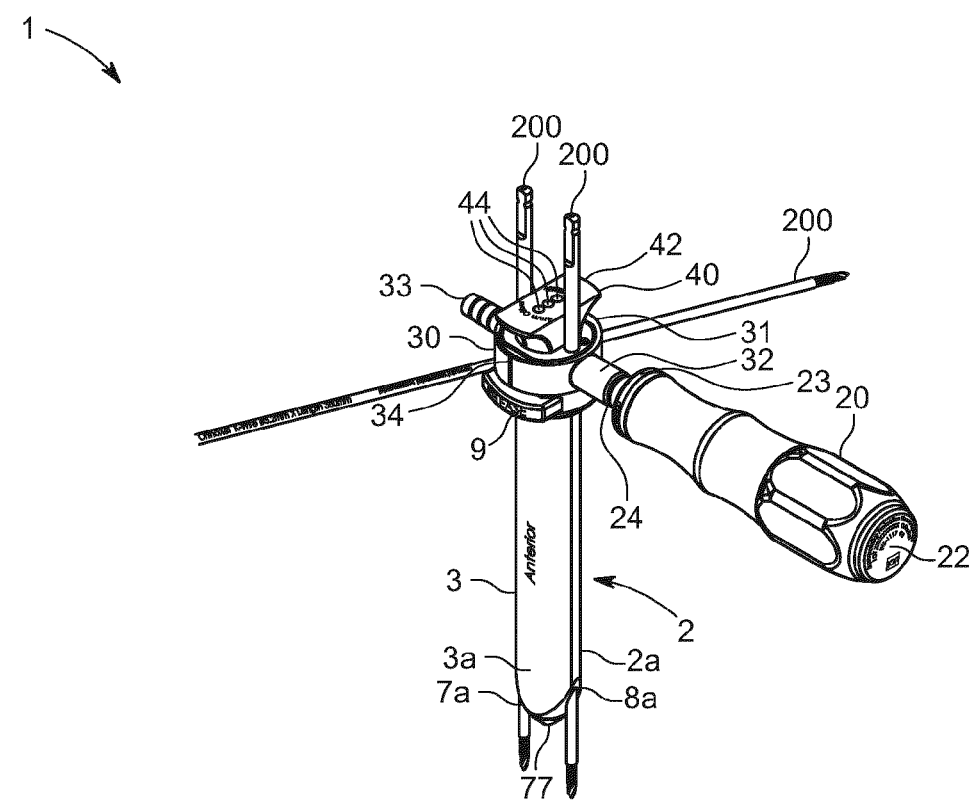

FIG. 2 illustrates an assembled view of the tibial suprapatellar entry portal system as shown in FIG. 1.

Figure 3:
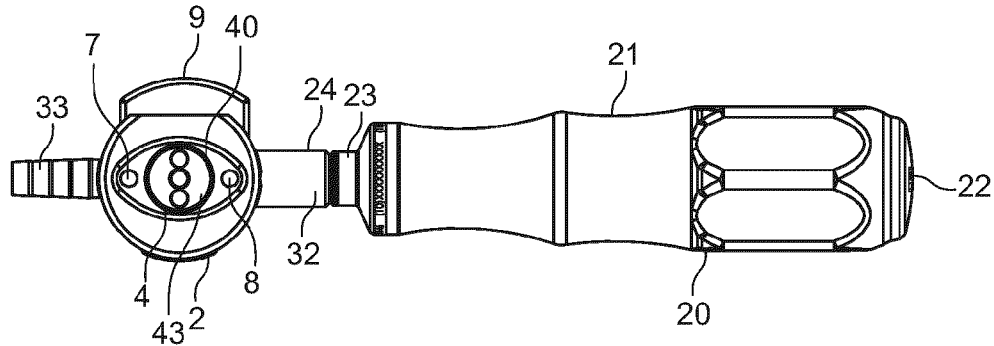

FIG. 3 illustrates a bottom view of the tibial suprapatellar entry portal system as shown in FIGS. 1 and 2.

Figure 4:
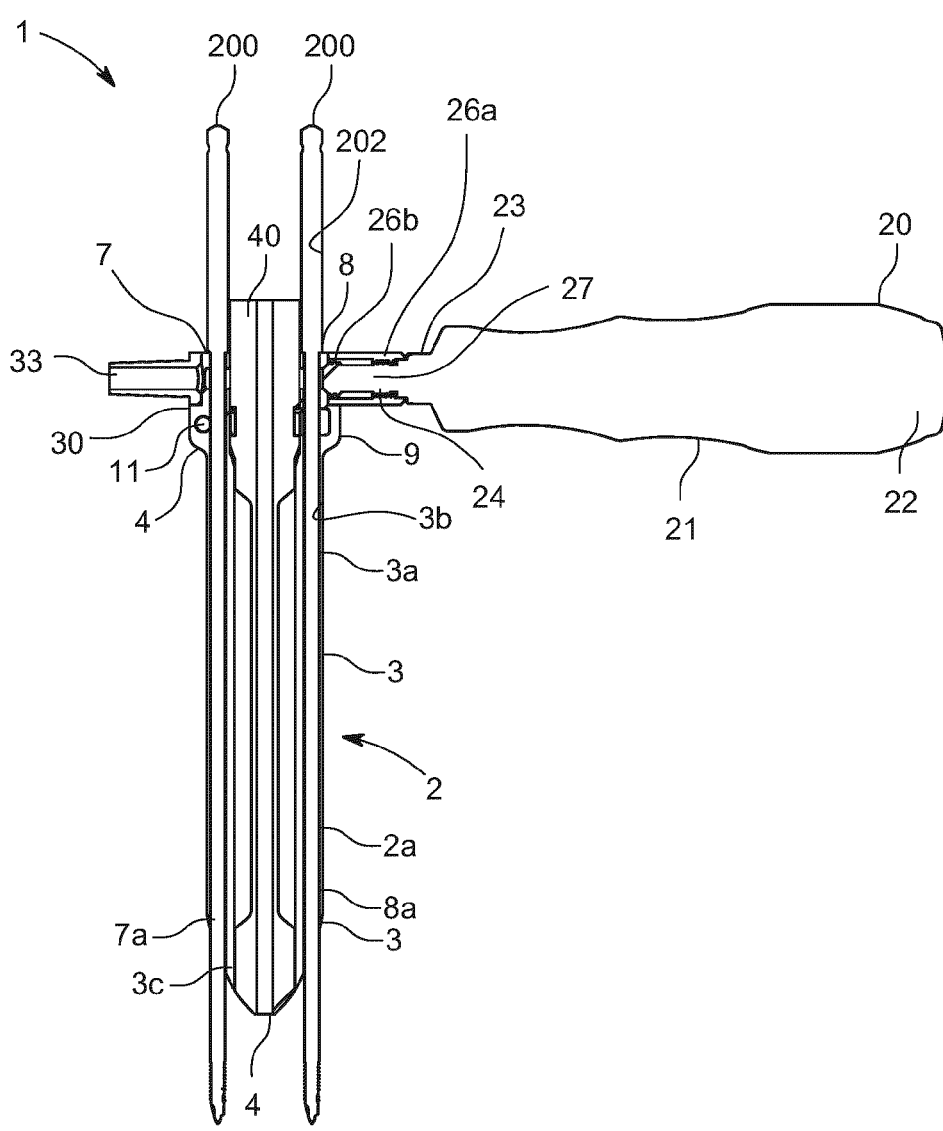

FIG. 4 illustrates a side sectional view of the assembled tibial suprapatellar entry portal system as shown in FIGS. 1 to 3.

Figure 5:
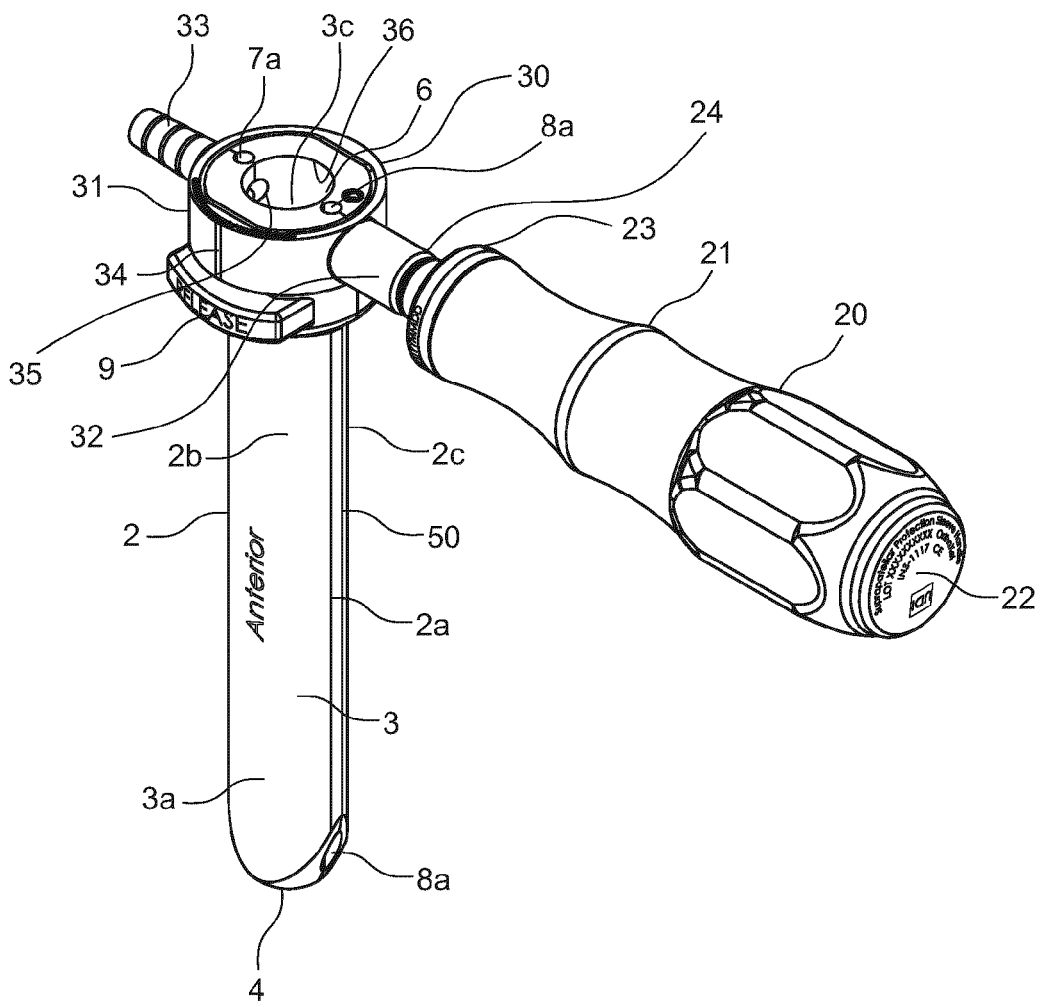

FIG. 5 illustrates one aspect of the entry portal and handle of the tibial suprapatellar entry portal system of the claimed invention wherein the sleeve has a longitudinal slit which is closed due to the tightening of the body of the locking mechanism.

Figure 6:
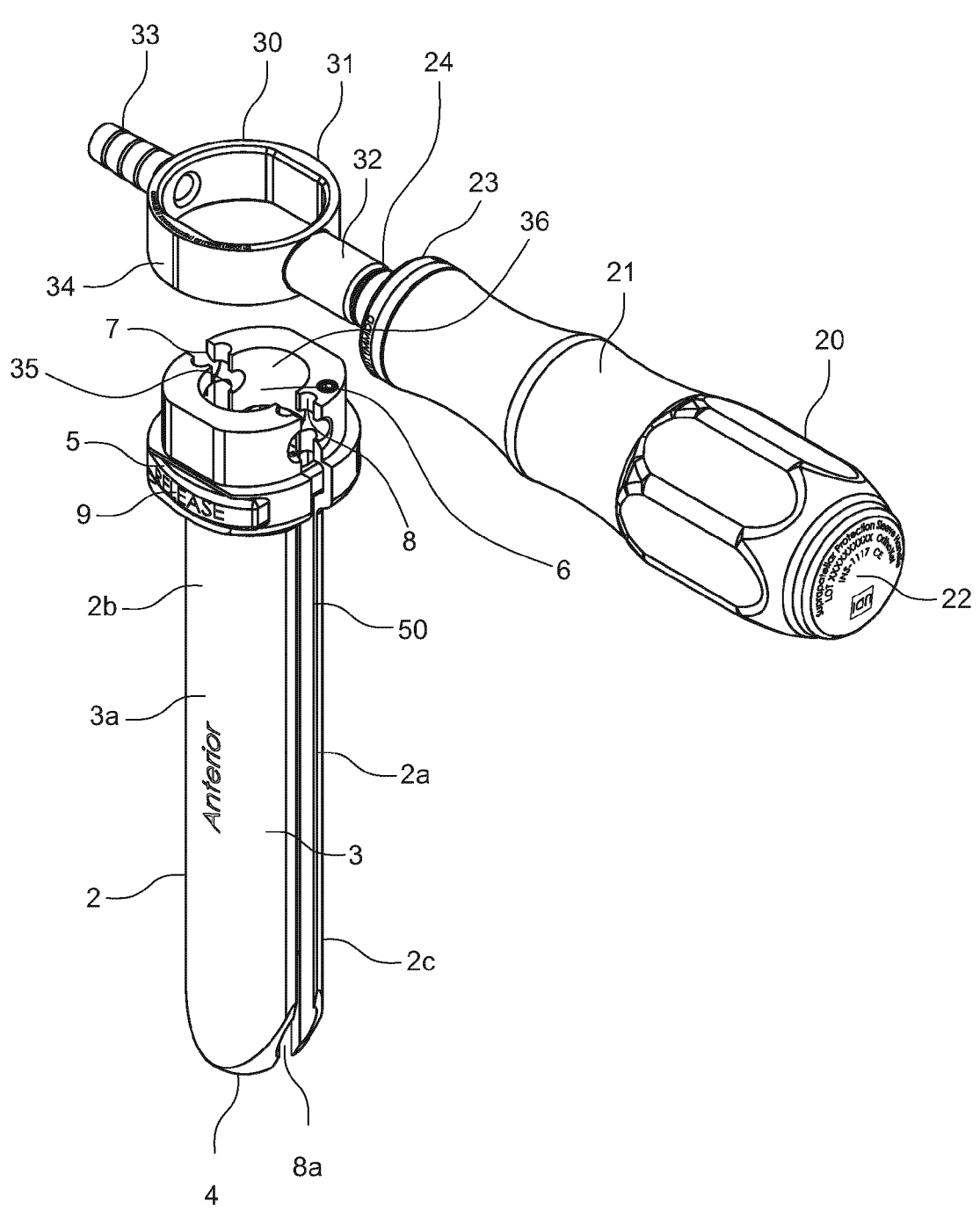

FIG. 6 illustrates a dissembled view of one aspect of the tibial suprapatellar entry portal system of the claimed invention wherein the sleeve has a longitudinal slit.

Figure 7:
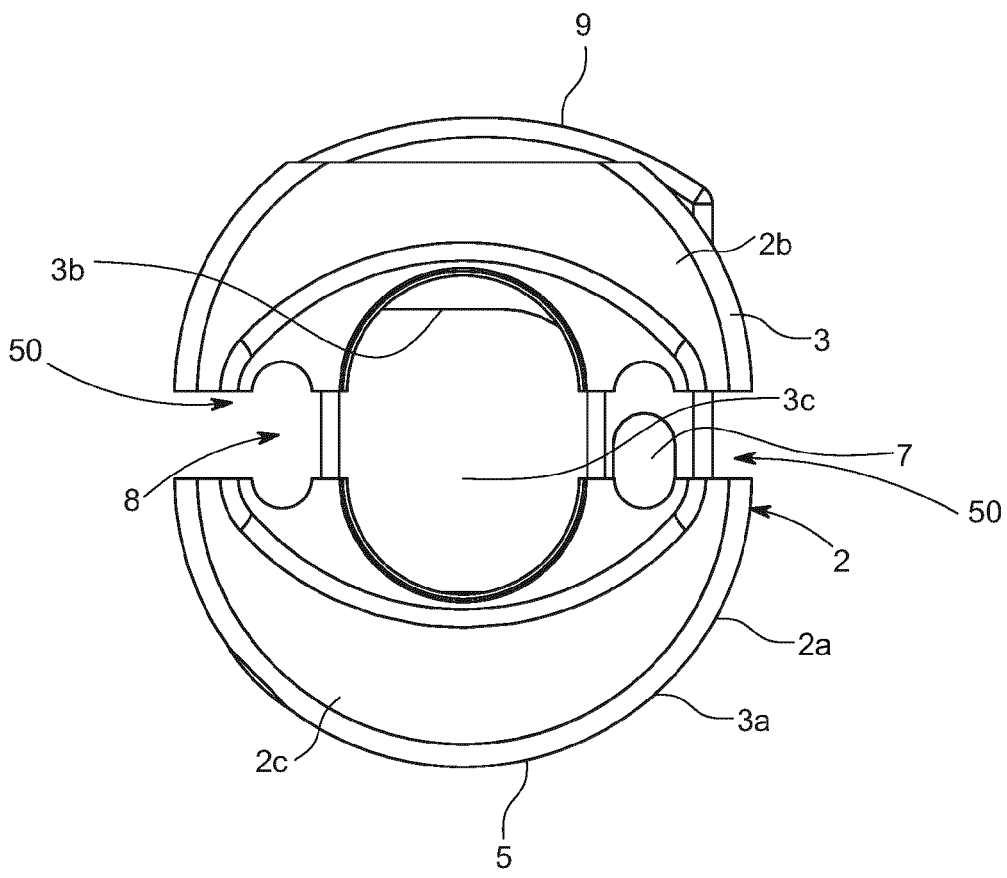

FIG. 7 illustrates a bottom view of the tibial suprapatellar entry portal system of FIG. 6.

Figure 8:
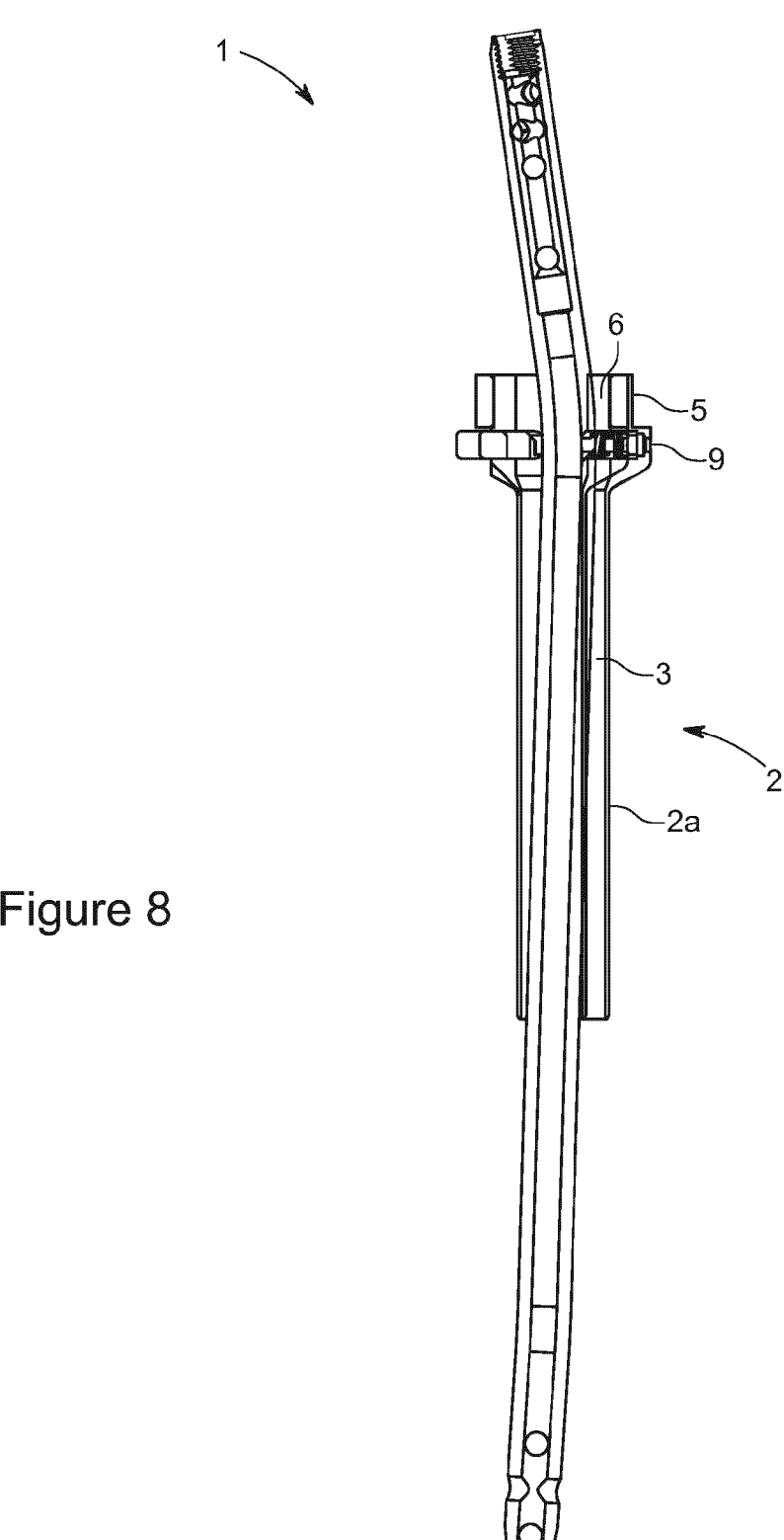

FIG. 8 illustrates a side profile sectional view of the tibial suprapatellar entry portal system of FIGS. 6 to 7, with an intramedullary nail in situ. The nail is allowed to pass through the central shaft of the sleeve. The handle and locking mechanism have been removed to show this.

Figure 9:
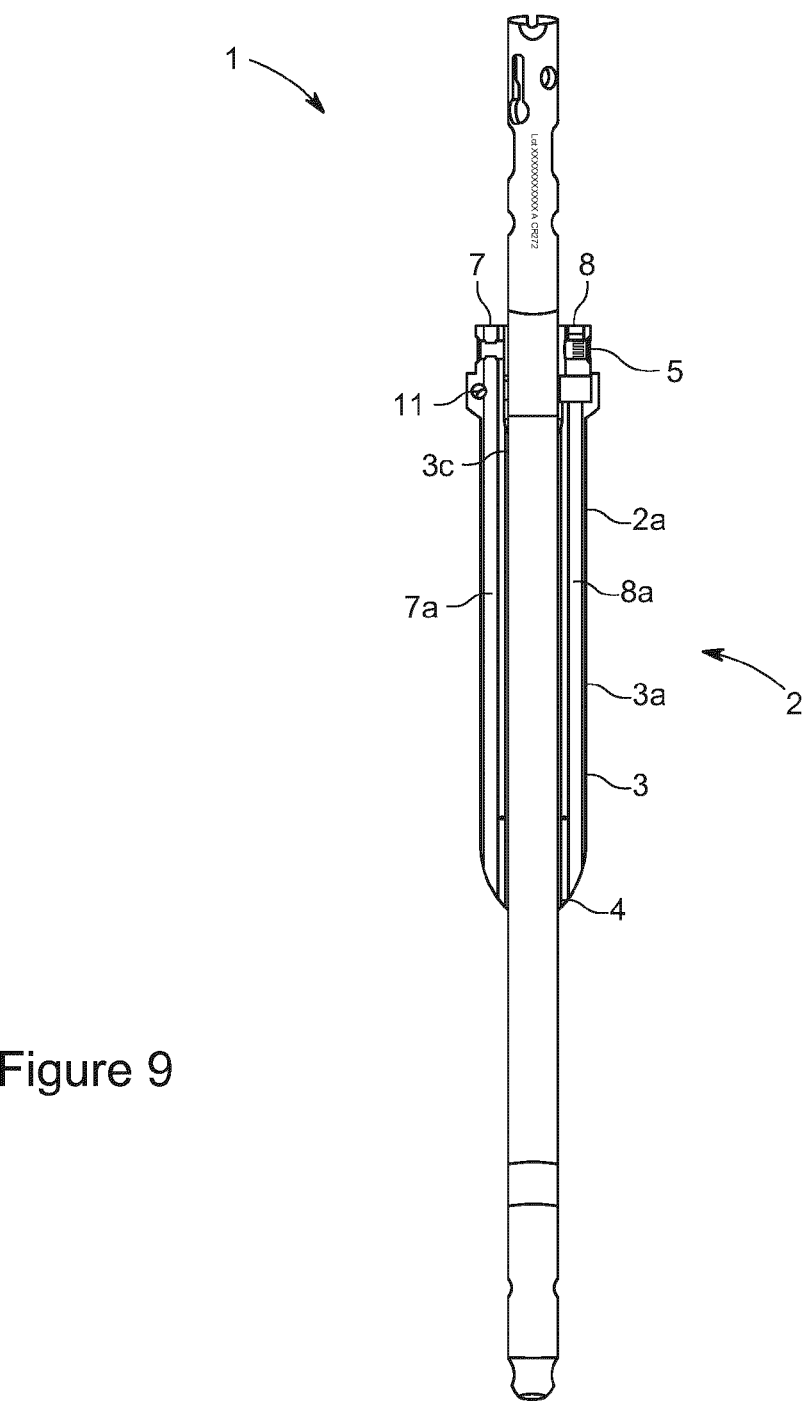

FIG. 9 illustrates a front sectional view of the tibial suprapatellar entry portal system of FIG. 8, with an intramedullary nail in situ.

Figure 10:
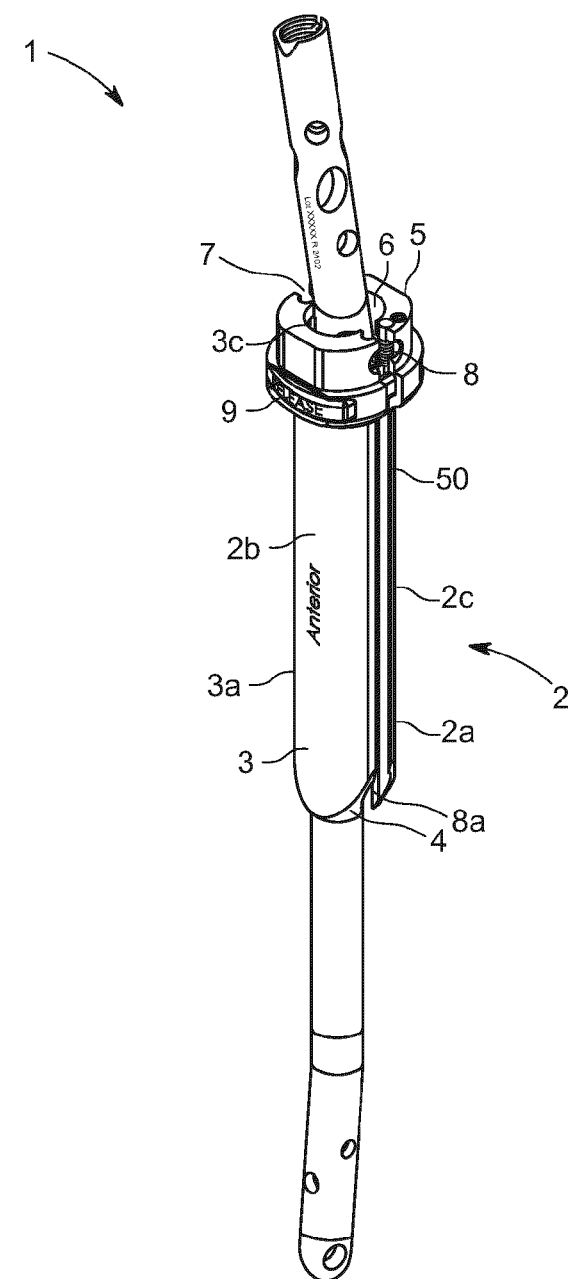

FIG. 10 illustrates an isometric view of the tibial suprapatellar entry portal system of FIG. 8 with an intramedullary nail in situ.

Figure 11:
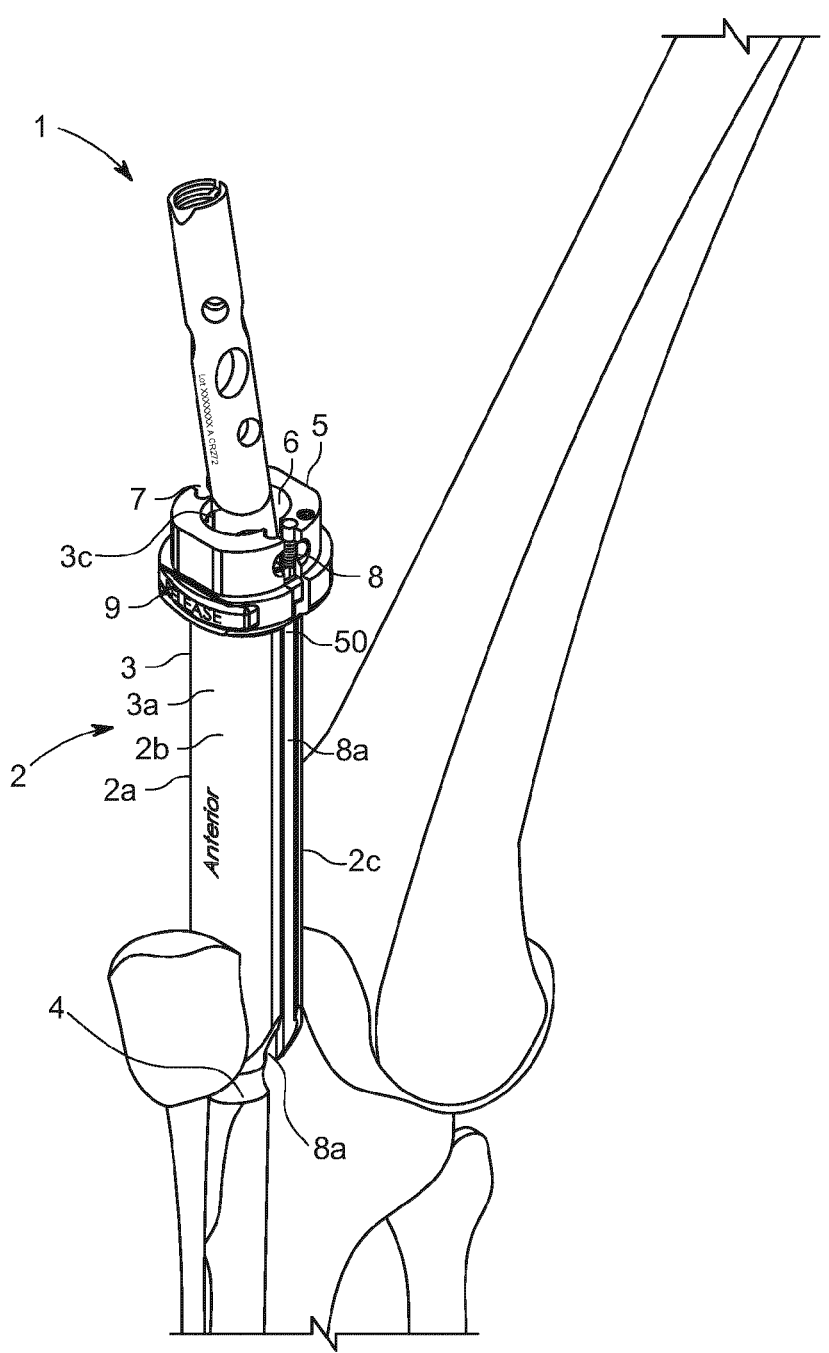

FIG. 11 illustrates the tibial suprapatellar entry portal system of 10 with an intramedullary nail inserted into a patellofemoral joint.

Figure 12:
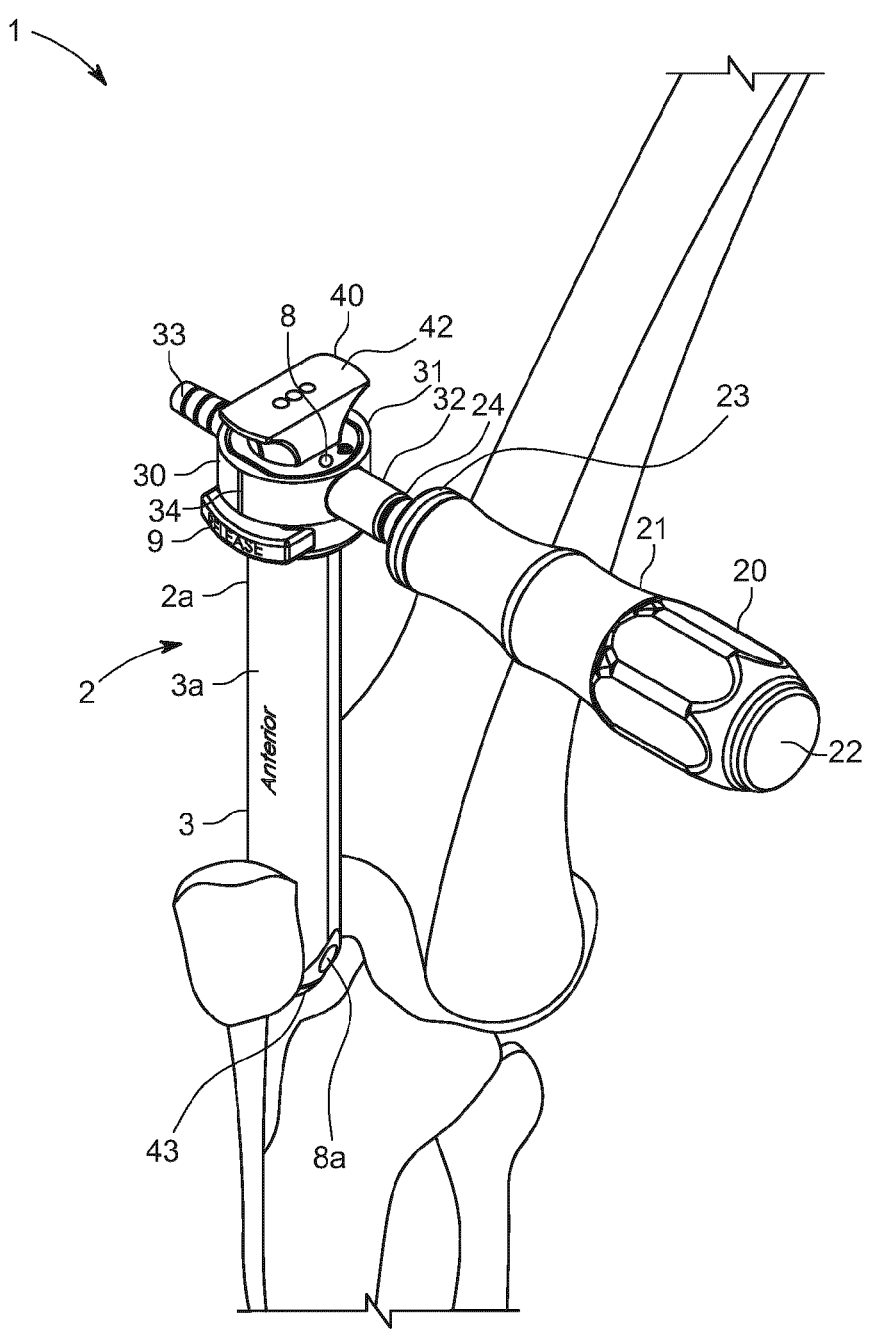

FIG. 12 illustrates the tibial suprapatellar entry portal system of FIG. 5 with an intramedullary nail and handle assembled in situ behind the patellar and in front of major leg bones.

Figure 13:
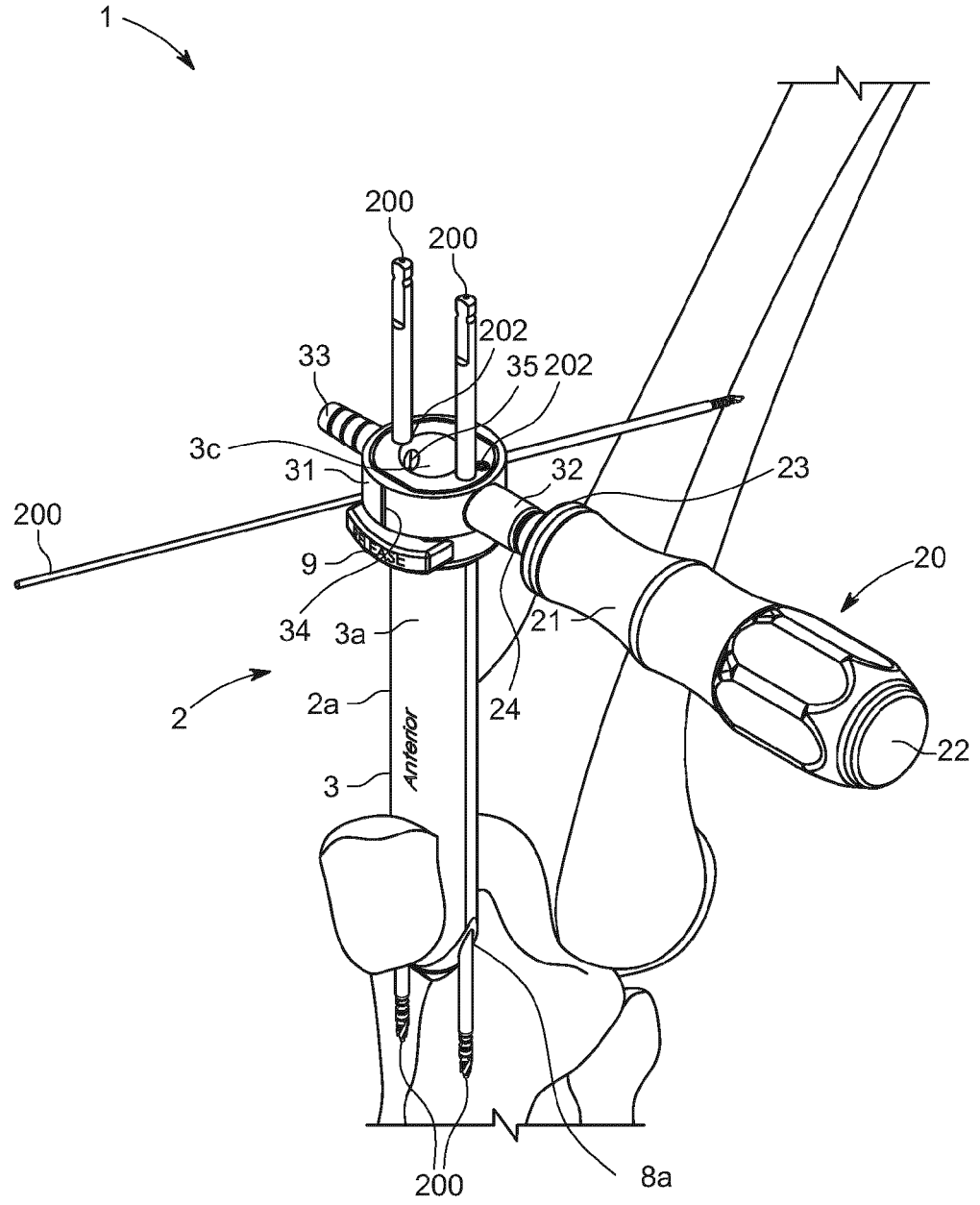

FIG. 13 illustrates an assembled view of the tibial suprapatellar entry portal system described in FIGS. 1 to 4 assembled in situ behind the patellar and in front of tibia and femur.

DETAILED DESCRIPTION OF THE DRAWINGS

To provide the customer the option to insert a tibial nail through the suprapatellar approach, the inventors provide herewith a system which provides protection to the anterior surface of the patients patellar during tibial opening and reaming and allows for anchoring of the claimed protection system during these steps, leaving the surgeons hands free to complete other surgical steps. Suprapatellar insertion has gained market traction due to its ease of approach to align and reduce fracture as it does not flex and tense the lower leg muscles during insertion of the intramedullary nail.

Referring now to the figures, where FIG. 1 illustrates a general embodiment of a tibial suprapatellar entry portal system of the present invention for suprapatellar insertion. Specifically, FIG. 1 illustrates an exploded view of the tibial suprapatellar entry portal system of the claimed invention and is generally referred to by reference numeral 1. The tibial suprapatellar entry portal system 1 illustrated here comprises a sleeve 2, an anchor pin (or k-wire) 200, and a trocar (or wire guide) 40. The sleeve 2 comprises a sheath 2a, a sleeve handle 20, and a locking mechanism 30. The assembled view of the tibial suprapatellar entry portal system 1 is shown in FIG. 2, with three anchor pins 200 in position, two engaged with the sleeve sheath 2a, and the third engaged with the sleeve handle 20.

The sheath 2a is made from a single piece of material. The sheath 2a comprises a longitudinal body 3 having an inner surface 3b and an outer surface 3a, which forms a shaft 3c configured to accommodate the trocar (or wire guide) 40; a distal end 4; and a proximal end 5. The longitudinal body 3 is typically substantially elliptical, with a substantially circular entry port 6 at the proximal end 5, and an exit port 77 at the distal end 4. The substantially elliptical shape of the longitudinal body 3 anatomically fits better between the femur and patellar, and also provides the cross section for the shaft 3c and two grooves or circular cannulations 7,8 for the anchor pin 200. The distal end 4 is typically tapered to match with the configuration or shape of the trocar 40 that is inserted inside the body 3 through the entry port 6.

The proximal end 5 is multifaceted and is continuous with a securing means 9, which is configured to interact with and engage the trocar 40. The proximal end 5 further comprises portals 7,8 which lead to circular cannulations 7a, 8a, respectively. The circular cannulations 7a, 8a lie either side of the shaft 3c and run down through the longitudinal axis of the body 3 between the outer and inner surfaces 3a, 3b and exit at the distal end 4. The circular cannulations 7a, 8a are configured to accommodate anchor wires or K-wires.

The proximal end 5 of the body 3 may further comprise a third anchor point 11 (see FIG. 4) that allows the anchor pins 200 or entry wires to insert into the femur when in use or into the tibia when in use (depending on the approach, suprapatellar or retrograde entry). Alternatively, the third anchor point 11 is on a proximal end 23 of the handle 20.

Anchor pins 200 have shoulders 202 that, when the anchor pins 200 are inserted into circular cannulations 7a, 8a, they create a mechanical hard stop by contacting the top surface of the portals 7,8 of the proximal end 5. This secures the distal end of the sheath 2a rigidly against the tibia or the femur and the shoulder 202 of the anchor pin 200.

The substantially elliptical shape of the sheath 2a is orientated with the wider major axis located in the medial-lateral direction of the coronal plane (that is, running in the same plan as the sleeve handle 20) to allow the space for circular cannulations 7a, 8a for anchor pins 200. This is to ensure that the width of the sleeve sheath 2a in the Anterior-Posterior directions relative to the sagittal plane (the same plane as the vertical axis of the central shaft 3c) is kept to a minimum to protect the patellar from damage during insertion of the sleeve sheath 2a and still allow for anchor pin 200 anchoring into the proximal end of the tibia.

In one aspect, the body 3 comprises two components, a first body component 2b and second body component 2c, that can be split along at least one channel 50 running parallel with and encroaching into the circular cannulations 7a or 8a (see FIGS. 6-7) to create a larger central shaft 3c. The channel 50 runs from the proximal end 5 to the distal end 4. The two body components 2b, 2c of body 3 can be open to the environment and remain open during use or assembled and closed. The two body components 2b, 2c of body 3 are assembled together, which are then narrowed and closed over by application of the locking mechanism 30 during use, thus improving the rigidity of the sleeve 2, but the shaft 3c can be opened fully again after the removal of the locking mechanism 30 from the sleeve 2, thereby increasing the central passage of the shaft 3c to a substantially slotted cross section to allow passage of an intramedullary nail, while protecting the posterior patella.

The sleeve handle 20 comprises a grip 21, a distal end 22, a proximal end 23 and a mating means 24. The grip 21 is typically ergonomic in design to aid the user to hold the sleeve handle 20 comfortably and without too much thought.

The proximal end 23 comprises the mating means 24, which is typically a male member 24a that engages with a female member 32 of the locking mechanism 30 (see FIGS. 1-6). The male member 24a further comprise a threaded portion 26 which mates with an equivalent threaded portion within the female member 32 of the locking mechanism 30. There can be two threaded portions 26a,b on the male member 24a spaced apart with a smooth surfaced area 27, with equivalent threaded portions with the female member 32. When the handle 20 having with one or more threaded portions 26a,b is threaded into the equivalent threaded portion of the female member 32 of the locking mechanism 30, the threaded portion 26 is pushed forward, engages with an indentation 10 in the proximal end 5, and is held in position by pressing against the indentation 10. The female member 32 engages with the sleeve handle 20 in two ways: (i) the sleeve handle 20 is unlocked relative to the sheath 2a when the mating means 24 is partially inserted into the female member 32 but allows the attachment of the sheath 2a and (ii) the sleeve handle 20 in a locked position relative to the sheath 2a when the sleeve handle 20 is advanced further into the female member 32 so that both threaded portions 26a and 26b are engaged, and the threaded portion 26 engages with an indentation 10 in the proximal end 5 of sheath 2a.

The locking mechanism 30 comprises a substantially circular body 31 having the female member 32 on one side thereof, and a vacuum tube connection member 33 on the opposite side which allows the connection of a surgical theatre vacuum tube. The vacuum tube connection member 33 has a cannulation that aligns with a sleeve cannulation 35 in the proximal end 5, this provides a vacuum suction to the shaft 3c of the sheath 2a when a vacuum is applied. The cannulation 35 runs from one side of the proximal end 5 to the other side if the proximal end 5, and through the centre of the indentation 10. Note the indentation 10 and the cannulation 35 are on both sides of the proximal end of the sheath 2a, directly opposite to one another. The reason for this is to allow the user to orientate the device 1 for left and right tibias. For example, the orientation of the sheath 2a in FIG. 1 is for a left leg tibia, while for a right leg tibia, the sheath 2a would be rotated 180 degrees.

In use, when an opening reamer (a drill which opens the proximal end of a tibia) is used through the shaft 3c in an up/down movement, this creates a suction force that removes cutting debris from the shaft 3c, without the surgeon having to do it manually. The sheath 2a allows the opening reamer to pass through the patellofemoral joint and drill out the top of the tibia without damaging the patella.

In one aspect, the sleeve handle 20 can also have a stop mechanism that engages the handle 20 and the locking mechanism 30 with the sheath 2a. The stop mechanism can be a sliding stop that can be pushed back and forth when the sleeve handle 20 and locking mechanism 30 are connected and secured to the sheath 2a. The stop mechanism will engage with the trocar 40 to remove axial translation of the trocar 40 relative to the sheath 2a when assembled.

In one aspect, the stop mechanism is a spring plunger and pin arrangement which permits the sleeve handle 20 to be moved about the locking mechanism 30 through 180°. The plunger is simply pulled back, the pin disengages with the trocar 40, the sleeve handle 20 is rotated about the circumference of the locking mechanism 30 to a desired position, and the plunger is released, thus allowing the pin to engage with the trocar 40 once more and securing it in position within the sheath 2a.

In one aspect, the sleeve handle 20 can be positioned between 0° to 60° relative to where the sleeve handle 20 connects with the locking mechanism 30. The sleeve handle 20 can be assembled with the locking mechanism 30 in two positions, first unlocked for assembly (see above) and then when the sheath 2a is in position, it can be quickly rotated to lock the locking mechanism 30 to the sheath 2a, making the sleeve 2 rigid.

In one aspect, the substantially circular body 31 of the locking mechanism 30 is hinged, forming a hinged clasp 34, which can be opened to allow the locking mechanism 30 to engage with the proximal end 5 of the sheath 2a. A clasp-type locking mechanism is opened to insert the sleeve 2a and then wrapped around it when closed.

In one aspect, the locking mechanism 30 can contain the locking features for both the sheath 2a and the trocar 40. For example, a side spring-loaded lock is contained within the body 31 of the locking mechanism 30 for the sheath 2a; or a rotating stop located on the female member 32 that interacts with the trocar 40 once the trocar 40 is inserted within the sheath 2a.

The trocar 40 comprises a proximal end 42 and a tip 43, separated by a longitudinal body 41. The trocar tip 43 provides a smooth surface for the leading edge of the assembly 2 that will not damage the patellar when in use. It also creates a smooth transition between the trocar 40 and the sheath 2a and eliminates any edges in the sleeve 2 that could catch and damage the patellar during insertion through the patellofemoral joint with the profile created when it is fully inserted into the sleeve 2. The trocar 40 comprises at least one central entry point guide 44 (see FIGS. 1-2) that allows passage of a first entry wire to act as a guide for later reaming (that is, drilling out the intramedullary canal of the tibia) when the trocar 40 is removed. The trocar 40 typically comprises a centrally positioned entry point guide and two outer entry point guides either side of the centrally positioned entry point guide. All entry point guides are assigned reference numeral 44. The proximal end of trocar 42 allows for at least one offset adjustment spacing to move the first entry wire from the centrally positioned entry point guide 44, to one of the outer entry point guides 44 (see FIGS. 1 and 2). The trocar 40 can rotate 360 degrees when fully inserted into the central shaft 3c of sheath 2a. The trocar 40 is used to allow the correct placement of entry wires in the tibia through the sleeve 2. The entry wire is then used to guide the opening reamer through the sheath 2a and into the top of the tibia when the trocar is removed from the central shaft 3c. The trocar 40 is retained by the securing means 9 in sheath 2a when in use and can easily be removed by pressing on the securing means 9 again. When assembled as the sleeve 2, the sheath 2a, the sleeve handle 20, and the locking mechanism 30 with the trocar 40 inserted into the shaft 3c, the sleeve 2 is initially placed into the entry point of the femur and behind the patella. The tip 43 protects the patella from damage or abrasion on entry.

In use, the locking mechanism 30 is placed on the distal end 5 of the sheath 2a. The sleeve handle 20 is then connected to the locking mechanism 30 via the male/female connectors 24a, 32, respectively. The sleeve handle 20 is tightened until the threaded portion 26 engages with the indentation 10 in the proximal end 5 of sheath 2a. The trocar 40 is then inserted into the shaft 3c of the sleeve 2 via the entry portal 6. As the trocar 40 is pushed into the shaft 3c, the body 41 of the trocar 40 pushes against the securing means 9, which compresses a spring, thus releasing the securing means 9, and allows the trocar 40 to pass into the shaft 3c of the sleeve 2. When fully inserted, the spring expands, and the securing means 9 locks the trocar 40 in a vertical position but permits the trocar 40 to rotate if required. Pushing in the securing means 9 allows the trocar 40 to be removed freely. The two anchor pins or k-wires 200 are inserted vertically, straight into the portals 7,8, through the circular cannulations 7a, 8a, and enter the top/proximal end of the tibia, securing the portal system 1 in place.

The hard stop or shoulder 202 on the anchor pins 200 stops them from entering too far into the tibia. When the anchor pins 200 are fully inserted, the shoulder 202 presses against the proximal end 5 of the sheath 2a, preventing the sheath 2a from backing out from the entry portal 6. The anchor pins 200 create a friction hold with the tibia, keeping them in position.

A third anchor pin 200 can be passed through the third anchor point 11 on the proximal end 23 of the handle 20 and into the femoral bone. Typically, the third anchor point 11 is at an angle of between about 0° to 20° relative to the horizontal axis of the central shaft 3c and about 5° to 15° relative to the vertical axis of the central shaft 3c. This adds extra anchorage to the user if needed and provides the user with multiple locking options. The angle of the third anchor point 11 is to ensure the hole aligns with the femur bone when the entire sleeve 2 is positioned in a patellofemoral joint, as show in FIG. 13. The preferred angles are about 10° relative to the horizontal axis of the central shaft 3c and about 8° relative to the vertical axis of the central shaft 3c.

One of the advantages of the system 1 is that the system 1 provides proximal tibia and femoral anchoring used either separately or together in one device. It provides a fully rigid anchoring construct that prevents rotation and back-out of the trocar 40. The system 1 allows for simple and quick assembly/disassembly of instruments. The system 1 provides a single system that can be used for either right or left leg insertion. The shape and finish of the protection sheath 2a gives aesthetic reassurance to the surgeon that the system 1 will not damage the patellar during use. The system 1 is profiled for suitable fit in the patellofemoral joint and the components of the sleeve 2 are made from same material and are rigid. The rigidity of the sleeve 2 provides the advantage of preventing rotation and back-out.

In the specification, the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A tibial suprapatellar and retrograde entry portal system comprising a sleeve having a substantially elliptical outline, an anchor pin and a trocar, wherein the sleeve comprises a sheath and a sleeve handle; the sheath having a proximal end with an entry port and a distal end having an exit port separated by a longitudinal body having an outer surface, an inner surface, and an internal shaft, and at least two circular cannulations extending from the proximal end to the distal end between the outer surface and inner surface of the longitudinal body for providing at least two anchor points, wherein the sheath is rigid and wherein the proximal end further comprises a third anchor point comprising an aperture suitable to accommodate the anchor pins or an entry wire, wherein the longitudinal body further comprises a channel running parallel with an in communication with either circular cannulation.

2. The tibial suprapatellar and retrograde entry portal system according to claim 1, wherein the proximal end further comprises portals configured to access the circular cannulations and a securing means configured to engage with the trocar.

3. The tibial suprapatellar and retrograde entry portal system according to claim 1, wherein the third anchor point is offset at about 5° to 11° in the X plane relative to the coronal plane and about 7° to 13° in the Y plane relative to the transverse plane, allowing securement to the femur during tibia suprapatellar use and the tibial during retrograde.

4. The tibial suprapatellar and retrograde entry portal system according to claim 1, wherein the circular cannulations are either parallel to the longitudinal axis of the body, are convergent from the proximal end to the distal end, or are divergent from proximal end to the distal end.

5. The tibial suprapatellar and retrograde entry portal system according to claim 1, wherein the channel runs in a medial-lateral plane relative to the sleeve handle and divides the sheath into a first body component part and a second body component part.

6. The tibial suprapatellar and retrograde entry portal system according to claim 5, further comprising a locking mechanism, the locking mechanism comprising a female member, wherein when the locking mechanism and the sleeve handle are assembled together with the sleeve, the first and second body component parts of the sheath are re-joined and the channel is closed.

7. The tibial suprapatellar and retrograde entry portal system according to claim 6 wherein when the locking mechanism is disassembled from the sleeve, the channel opens, and the first and second body component parts divide apart.

8. The tibial suprapatellar and retrograde entry portal system according to claim 7, wherein when the first and second body component parts-divide apart, either one of the body component parts can be removed and the remaining body component part acts as a patellar shield.

9. The tibial suprapatellar and retrograde entry portal system according to claim 5, wherein the sleeve handle comprises a grip, a distal end, a proximal end and a mating means attached to the proximal end, wherein the mating means is typically a male member that is configured to engage with the female member of the locking mechanism.

10. The tibial suprapatellar and retrograde entry portal system according to claim 9, wherein the male member further comprises a threaded portion which is configured to mate with an equivalent threaded portion within the female member of the locking mechanism.

11. The tibial suprapatellar and retrograde entry portal system according to claim 6, wherein the locking mechanism comprises a substantially circular body accommodating the female member on one side thereof and a vacuum tube connection member on the opposite side, and an indentation adapted to receive the mating means and create a mechanical or friction hold with the sheath to secure the locking mechanism.

12. The tibial suprapatellar and retrograde entry portal system according to claim 11, wherein the substantially circular body is configured to comprise a hinge forming a hinged clasp.

13. The tibial suprapatellar and retrograde entry portal system according to claim 6, wherein the locking mechanism further comprises a stop mechanism actuated by a sliding mechanism or a spring-loaded plunger and pin mechanism.

14. The tibial suprapatellar and retrograde entry portal system according to claim 1, wherein the anchor pin has a threaded portion at a distal end, and a proximal end having a larger diameter than the distal end, creating a stop configured to engage with the proximal end of the sheath.

15. The tibial suprapatellar and retrograde entry portal system according to claim 6, wherein the sleeve handle is adjustable to swivel about 180° around the locking mechanism.

16. The tibial suprapatellar and retrograde entry portal system according to claim 1, wherein the trocar comprises an insertion guide at a proximal end thereof and a tip at a distal end thereof, separated by a longitudinal body.

17. The tibial suprapatellar and retrograde entry portal system according to claim 16, wherein the insertion guide comprises at least one entry point guide at the proximal end.

18. The tibial suprapatellar and retrograde entry portal system according to claim 1, wherein the sleeve is composed of a durable, yet rigid material selected from polypropylene, polyethylene (PE), polyethylene terephthalate copolymer (PETG), amorphous polyethylene terephthalate (APET), stainless steel and titanium, preferably, the material is stainless steel, titanium, or a combination thereof.

19. A kit of parts for use in repairing a bone fracture, the kit comprising the tibial suprapatellar and retrograde entry portal system as claimed in claim 1.

* * * * *